(12) United States Patent
Yoon

(10) Patent No.: US 6,645,533 B2
(45) Date of Patent: Nov. 11, 2003

(54) ATP SYNTHESIS ACTIVATOR CONTAINING A MIXTURE OF HERBS

(76) Inventor: JungMan Yoon, 1-2-30, Oyamadai, Setagaya-ku, Tokyo 158-0086 (JP)

( * ) Notice: Subject to any disclaimer, the term of this patent is extended or adjusted under 35 U.S.C. 154(b) by 62 days.

(21) Appl. No.: 10/005,122

(22) Filed: Dec. 7, 2001

(65) Prior Publication Data

US 2003/0039707 A1 Feb. 27, 2003

(30) Foreign Application Priority Data

Apr. 16, 2001 (JP) ........................................ 2001-117327

(51) Int. Cl.$^7$ ........................ A61K 35/78; A01N 65/00
(52) U.S. Cl. ........................ 424/728; 424/725; 424/756; 424/764
(58) Field of Search .............................. 435/390, 410; 424/725, 728, 756, 764

(56) References Cited

U.S. PATENT DOCUMENTS

| | | | | |
|---|---|---|---|---|
| 4,283,429 A | * | 8/1981 | Todd, Jr. et al. | 426/250 |
| 4,285,981 A | * | 8/1981 | Todd, Jr. et al. | 426/250 |
| 4,315,947 A | * | 2/1982 | Todd, Jr. et al. | 426/250 |
| 4,343,823 A | * | 8/1982 | Todd, Jr. et al. | 426/250 |
| 5,422,136 A | * | 6/1995 | Fuisz | 426/658 |
| 5,472,731 A | * | 12/1995 | Fuisz | 426/641 |

OTHER PUBLICATIONS

Calera et al, "Biochemically Active Sesquiterpene Lactones from Ratibida Mexicana", Phytochem., vol. 40, No. 2, pp. 419–425, 1995.*

Tanaka, M., *Influence of KIPPO On Adverse Affects At Time of Anticancer Irradiation and Chemotherapy*, 3$^{rd}$ Annual Meeting of the Japanese Society for Complementary & Alternative Medicine & Treatment, Nov. 4, 2000, Tokyo, Japan.

* cited by examiner

Primary Examiner—David M. Naff
Assistant Examiner—Deborah K. Ware
(74) Attorney, Agent, or Firm—Birch, Stewart, Kolasch & Birch, LLP

(57) ABSTRACT

An ATP synthesis activator is provided, which allows the promotion of ATP synthesis in the body and results in an increased ATP level in the body for a long period of time. The ATP synthesis activator comprises, as an active ingredient, a mixture of a plurality of herbs having an ion-exchange capacity. It may stimulate electron generation in the body and hence results in an improved ATP synthesis activity due to the generated electrons, because dietary fiber contained in the herbs has an ion-exchange capacity. Preferably, the herb mixture includes thyme, rosemary, turmeric, fennel, grape seeds, dandelion, and *Acanthopanax senticosus*. Also the composition is useful for treating immune deficiency diseases.

1 Claim, 2 Drawing Sheets

Change in ATP level before and after administration of ATP synthesis activator

ATP SYNTHESIS ACTIVATOR CONTAINING A MIXTURE OF HERBS

FIELD OF THE INVENTION

The present invention relates to an ATP synthesis activator for promoting the synthesis of ATP (adenosine triphosphate) used as an energy source for living cells.

BACKGROUND OF THE INVENTION

ATP is a nucleotide molecule having three phosphate molecules attached to a 5-hydroxyl group on a ribose of adenosine, which has a formal name of adenosine 5'-triphosphate. ATP, which was found by Fiske et al. in 1929, is a compound widely present in any living tissue or organism including animal's muscles or yeast cells.

ATP has two high-energy phosphate bonds per molecule, thereby yielding a free energy of about 7.3 kcal/mol when hydrolyzed around a neutral pH and itself being converted into adenosine diphosphate. Thus, the energy yielded from ATP hydrolysis allows nucleic acid synthesis as well as various metabolisms including protein metabolism, carbohydrate metabolism and/or lipid metabolism. A compound having a phosphate ester bond provided from ATP will enter an "activated state" to contribute to various synthesis reactions.

ATP production techniques utilizing chemical reactions are broadly divided into two groups: an enzyme-catalyzed technique using a phosphoenzyme and a fermentation-based technique using glycolysis in yeast cells.

An enzyme used in such an enzyme-catalyzed technique includes acetate kinase, carbamate kinase and creatine kinase, and in these cases, acetyl phosphate, carbamyl phosphate and creatine phosphate are used as a phosphate donor, respectively. In an embodiment of this technique in a bioreactor, there has been developed a procedure using acetate kinase and adenylate kinase isolated in a pure form from a thermophilic bacterial strain, Bacillus stearothermophilus. On the other hand, a fermentation-based technique using glycolysis in yeast cells involves ATP production through phosphorylation at a substrate level. This technique is based on the fact that two ATP molecules can be generated when one molecule of glucose is metabolized into two molecules of ethanol and two molecules of $CO_2$.

In the pharmaceutical and food fields, however, there has been no activator known to be particularly effective in promoting ATP synthesis in the body. The promotion of ATP synthesis in the body can eliminate the need for oral ATP administration to increase ATP level in the body. Further, prolonged promotion of ATP synthesis may contribute to health maintenance and the like.

SUMMARY OF THE INVENTION

In view of the prior circumstances mentioned above, the object of the present invention is to provide an ATP synthesis activator which allows the promotion of ATP synthesis in the body and results in an increased ATP level in the body for a long period of time.

Our research efforts were directed to achieving the above object, and we have found that when electron generation in the body can be stimulated, ATP synthesis can be effectively promoted by the generated electrons, thereby finally completing the invention.

More specifically, the ATP synthesis activator of the present invention comprises, as an active ingredient, a mixture of a plurality of herbs having an ion-exchange capacity.

The ATP synthesis activator of the present invention can stimulate electron generation in the body and hence results in an improved ATP synthesis activity due to the generated electrons, because dietary fiber contained in the herbs has an ion-exchange capacity.

The ATP synthesis activator of the present invention preferably generates electrons in the body to give a potential of −300 mV or less.

Further, the ATP synthesis activator of the present invention preferably comprises at least one or more herbs selected from thyme, rosemary, turmeric, fennel, grape seeds, dandelion, and Acanthopanax senticosus.

DETAILED DESCRIPTION OF THE INVENTION

Figure 1:
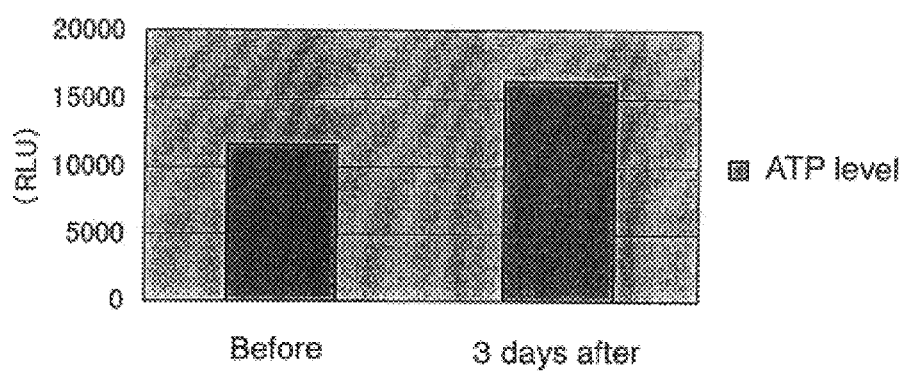
FIG. 1 shows ATP levels measured before and 3 days after the administration of an ATP synthesis activator.

The ATP synthesis activator of the present invention will be described below in more detail.

The ATP synthesis activator comprises a mixture of a plurality of herbs. Any type of herb may be used in combination so long as it contains dietary fiber having an ion-exchange capacity. Examples of herbs able to be used include thyme, rosemary, turmeric, fennel, grape seeds, dandelion, and Acanthopanax senticosus. In particular, among these herbs, at least one or more herbs may be selected and combined for use in the present invention.

More specifically, in a case where all of thyme, rosemary, turmeric, fennel, grape seeds, dandelion, and Acanthopanax senticosus are used, they are preferably combined to give a mixture containing 8–12% by weight of thyme, 8–12% by weight of rosemary, 8–12% by weight of turmeric, 13–17% by weight of fennel, 13–17% by weight of grape seeds, 8–12% by weight of dandelion, and 25–35% by weight of Acanthopanax senticosus, based on the total weight of the mixture which is set to 100% by weight.

When administered into the body, this ATP synthesis activator exhibits an ion-exchange capacity attributed to dietary fiber contained in the herbs, thereby generating electrons in the body. More specifically, the ATP synthesis activator preferably generates electrons in the body to give a potential of −300 mV or less, thereby enabling the activation of ATP synthesis in the body. As used herein, the activation of ATP synthesis means that a group administered with the ATP synthesis activator shows a significantly increased ATP level in the body when compared with a non-administered group. ATP levels in the body may be quantitatively assayed using an ATP detector (commercially available from Microtec Co., Ltd. under the trade name of HACCP-LIGHT38).

The ATP synthesis activator can be prepared, for example, by subjecting these herbs to dry sterilization at 160° C., followed by mixing, and thereafter processing the sterilized herbs into powder in a mill and then shaping the resulting powdered herb mixture into any given form.

The ATP synthesis activator of the present invention can improve ATP synthesis activity in mitochondria present in cells forming living organisms. This ATP synthesis activator can promote ATP synthesis in mitochondria to prevent metabolic waste products and toxins to be accumulated in the body. The ATP synthesis activator can therefore prevent cell aging and necrosis.

The ATP synthesis activator of the present invention can also help maintain blood hydrogen ion concentration at a given level, thereby keeping a blood pH of 7.4±0.2. The ATP synthesis activator can therefore improve ATP synthesis activity in the body because it can keep blood pH at 7.4±0.2.

The ATP synthesis activator of the present invention may be used, for example, in order to ameliorate a symptom caused by a decreased ATP synthesis activity in the body. Examples of a symptom caused by a decreased ATP synthesis activity in the body include immune deficiency diseases, e.g., cancer, rheumatism, atopic dermatitis, collagen disease, asthma and pollinosis; adult diseases, e.g., diabetes, myocardial infarction and brain infarction; dementia, Alzheimer's disease and Parkinson's disease. The ATP synthesis activator may be used for the amelioration of any symptom caused by a decreased ATP synthesis activity, not limited to the symptoms listed above. The ATP synthesis activator may also be used to ameliorate any one of the above symptoms or combinations thereof.

The ATP synthesis activator of the present invention may be administered orally or parenterally, preferably parenterally. The ATP synthesis activator may take any dosage form, such as tablets, granules, capsules and powders. The ATP synthesis activator may be administered at an appropriate dose selected depending on the age of a patient and the condition of disease. An effective daily dose may be selected within the range from 5.5 mg to 17.5 mg per kg of the body weight. Alternatively, the dose may be selected per patient within the range from 400 to 600 mg/body, preferably 600 to 800 mg/body, and more preferably 800 to 1200 mg/body. However, the dose of the ATP synthesis activator of the present invention is not particularly limited to these ranges.

The ATP synthesis activator may be administered to a patient at any stage, including before or after the development of a decrease in ATP synthesis activity. It may also be administered at a stage where the development of the above-mentioned symptom(s) is observed or predicted in the patient.

The ATP synthesis activator of the present invention may be formulated in a general manner (Remington's Pharmaceutical Science, latest edition, Mark Publishing Company, Easton, USA). The formulation may further comprise pharmaceutically acceptable carriers and/or additives.

EXAMPLES

The ATP synthesis activator according to the present invention will be further described in the following examples. The examples are provided for illustrative purposes only, and are not intended to limit the scope of the invention.

Example 1

Preparation of ATP Synthesis Activator

In this example, an ATP synthesis activator was prepared by mixing herbs in accordance with the following composition:

| | |
|---|---|
| Thyme | 10% by weight, |
| Rosemary | 10% by weight, |
| Turmeric | 10% by weight, |
| Fennel | 15% by weight, |
| Grape seeds | 15% by weight, |
| Dandelion | 10% by weight, and |
| Acanthopanax senticosus | 30% by weight. |

To prepare an ATP synthesis activator, first, these herbs were washed with tap water and dried using a spray dryer at 160° C. for dry sterilization. Next, the herbs were weighed and mixed in a V-shaped mixer to give a mixture having the above composition. The resulting herb mixture was processed into powder in a mill (power mill P-7 model, product of SYOWA chemical machine manufactory corporation) and then shaped into tablets using a tablet machine (product of HATA manufactory corporation), thereby preparing an ATP synthesis activator.

Test Example A

In this test example, the ATP synthesis activator prepared as stated above was used to perform an activation test for ATP synthesis in a human body. The test was performed on five men of ages 48 to 62 (average age: 55).

In this test, each of the above five men was orally administered with the ATP synthesis activator, twice a day, at a daily dose of 10 g for 3 consecutive days, along with 100 cc mineral water.

ATP levels were determined before and 3 days after starting the administration of the ATP synthesis activator by using an ATP detector HACCP-LIGHT38 (Microtec Co., Ltd.). Prior to ATP detection, the men brushed their teeth and then washed their mouths out three times. Subsequently, they further washed their mouths out with a commercially available mineral water that had been found to contain no ATP. About 20 ml of mineral water from each man was transferred into a clean cup for use as a sample. An aliquot (100 μl) of each sample was taken into a detection tube and mixed with two drops of a luminescent reagent specifically prepared for the detector to determine ATP level of each sample using the detector.

FIG. 1 shows a comparison of ATP levels between before and 3 days after the administration of the ATP synthesis activator. Although some individual differences were found in ATP levels, as shown in FIG. 1, the average ATP level was 11615 RLU before administration, while the average ATP level was 16319 RLU after administration, thereby indicating a significant difference before and after administration. This result indicates that the administration of the ATP synthesis activator results in an improved ATP synthesis activity in a human body.

Test Example B

In this test example, the ATP synthesis activator prepared as stated above was evaluated for its oxidation-reduction property. First, a rusted 10-yen coin made of copper and a solution containing 10 tablets of the ATP synthesis activator (400 mg per tablet) in 100 cc tap water (Minato-ku, Tokyo, Japan) were prepared. Next, the 10-yen coin was contacted with the above solution on one surface of the coin and then allowed to stand for 20 hours. After 20 hours, the surface of the coin contacted with the solution was observed, thereby indicating that the copper coin recovered its original luster after contacting with the ATP synthesis activator for 20 hours, whereas the coin was fully rusted at the time of starting the test.

In addition, tap water, prior to preparation of the solution, was measured for its oxidation-reduction potential, which was then used as a correction potential. The solution was measured for its pH and oxidation-reduction potential before and 20 hours after contacting with the coin. In both cases, the oxidation-reduction potential was measured using an ORP meter (commercially available from Toa Electronics Ltd. under the trade name of RM-12P) and the pH was measured using a pH meter (commercially available from HANNA under the trade name of PICCOLO HI 1280). The results are shown in Table 1.

TABLE 1

|  | Water temp. | Correction potential | Meter potential | Oxidation-reduction potential | pH |
|---|---|---|---|---|---|
| Before | 23° C. | +208 mV | +268 mV | +476 mV | 7.1 |
| 20 hours after | 23° C. | +208 mV | −526 mV | −318 mV | 7.4 |

Table 1 shows that the oxidation-reduction potential changes from +476 mV (at the time of starting the test) to −318 mV (after 20 hours), while the pH changes from 7.1 to 7.4. This suggests that the use of the above solution permits rust removal even at a neutral pH and that when dissolved in water, the ATP synthesis activator provides electrons in the aqueous solution over the course of time, thereby resulting in the reduction of rust formed on metal.

Test Example C

The ATP synthesis activator was examined for its antitumor effect in a mouse model with Colon 26 carcinoma.

An 8-week-old BALB/C male mouse (microbiological grade: SPF) was purchased from CLEA Japan, Inc. for use in the preparation of a mouse model with Colon 26 carcinoma. This mouse was implanted with mouse colon carcinoma cells (Colon 26) by subcutaneous administration in the abdomen to prepare a mouse model with Colon 26 carcinoma. The mouse colon carcinoma cell line, Colon 26, is derived from the carcinoma cell line that has been established by repeating the intrarectal administration of N-methyl-N-nitroso-uretan to a BALB/C mouse.

On day 21 after the subcutaneous implantation, a tumor block was removed from the mouse with Colon 26 carcinoma and separated into individual cells, which were then suspended in sterilized physiological saline. The resulting suspension was subcutaneously administered to each of six 8-week-old BALB/C male mice in the abdomen at a tumor cell density of $1 \times 10^5$ cells/100 µl per mouse. Each mouse was bred under the following conditions:

| | |
|---|---|
| Preset temperature and humidity: | 24 ± 1° C. and 66 ± 6% |
| Air conditioning system: | 70% return-air system |
| Lighting time: | 12-hour cycle under automatic control (from 8:00 am to 8:00 pm) |
| Breeding system: | plastic cage |
| Feed: | sterilized CA-1 pellet (CLEA Japan, Inc.) |
| Water to be supplied: | distilled water |

In this test, the six mice thus prepared were divided into two groups of 3 mice, i.e., a control group and a test group. Each mouse in the test group was orally administered through a gastric tube with the ATP synthesis activator dissolved in distilled water at a dose of 200 mg/kg for 14 consecutive days. Each mouse in the control group was orally administered with distilled water. The administration of the ATP synthesis activator started the next day after preparing the mice with Colon 26 carcinoma. In both groups, each mouse implanted with tumor cells showed no visual or palpable change at the implanted site until 4 days after implantation. From 6 days after implantation, however, the mouse tended to show skin swelling in the abdomen associated with tumor cell growth and further showed emaciation and piloerection on day 14. In particular, a mouse with a large tumor volume showed decreased motility and sometimes crouched down on day 14.

After breeding for 15 days, each mouse was sacrificed by cervical dislocation and then assayed for its tumor volume and 1L-12 and TNF-α levels. A vernier caliper (Plate Reader M-2300, NUNK) was used to determine a tumor volume according to the following equation: tumor volume (mm$^3$)= (tumor length)×(tumor width)$^2$×0.4. IL-12 and TNF-α levels were assayed as follows. The spleen was removed from each mouse and suspended in RPMI-1640 medium supplemented with 10% FC8. ConA was added to the resulting spleen cell suspension ($2 \times 10^8$ cells/ml) at a concentration of 5 µg/ml, followed by culturing at 37° C. in a 5% $CO_2$ incubator (YAMATO) for 24 hours. The culture supernatant was then assayed for its IL-12 and TNF-α levels using a Cytescreen kit (BIOSOURCE). These experiments were performed under air conditioning (70% return-air system) at a temperature of 26±1° C. and at a humidity of 66±6%.

Figure 2:
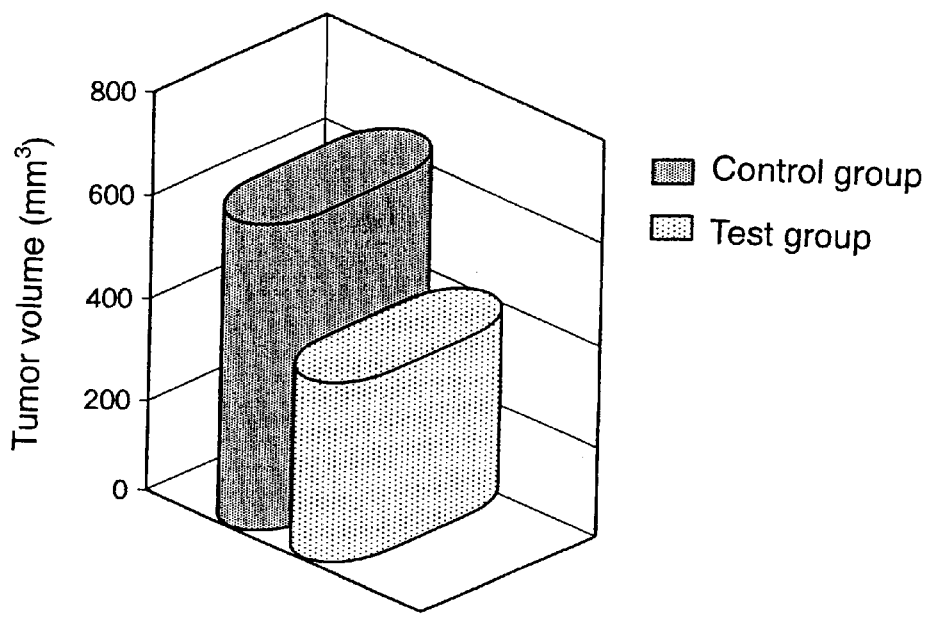
FIG. 2 shows a comparison of tumor volumes between an ATP synthesis activator-administered group (test group) and a control group.
Figure 3:
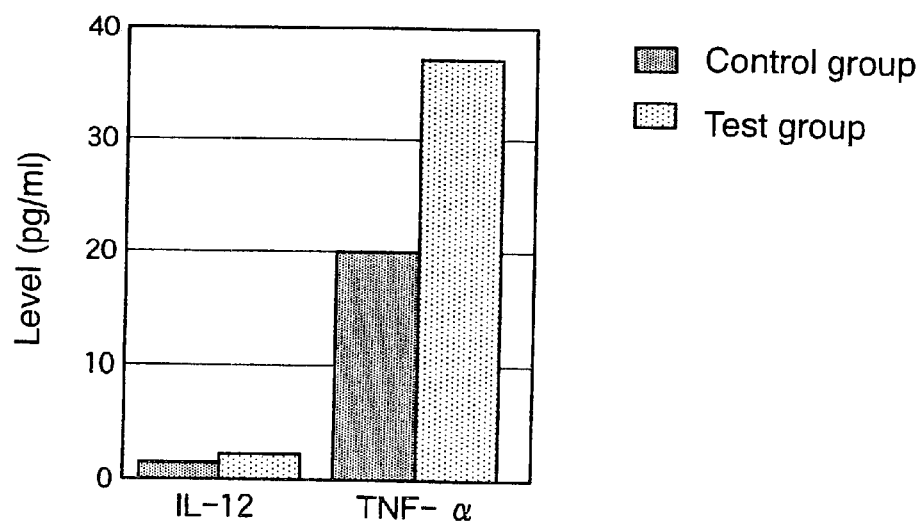
FIG. 3 shows a comparison of IL-12 and TNF-α levels between an ATP synthesis activator-administered group (test group) and a control group.

FIG. 2 shows a comparison of tumor volumes between the ATP synthesis activator-administered group (test group) and the control group. FIG. 3 shows a comparison of IL-12 and TNF-α levels between the ATP synthesis activator-administered group (test group) and the control group.

Although some individual differences were found in tumor volumes, as shown in FIG. 2, the control group had an average tumor volume of 626.38 mm$^3$, while the test group had an average tumor volume of 330.02 mm$^3$, thereby indicating a significant difference between these two groups. This result indicates that the administration of the ATP synthesis activator provides an inhibitory effect on tumor volume increase.

As shown in FIG. 3, there was no significant difference in IL-12 (apoptosis inducer) levels between the test group and the control group. In contrast, a significant difference was found in TNF-α (tumor necrosis factor) levels between the test group (37.46 pg/ml) and the control group (20.45 pg/ml). These results suggest that the administration of the ATP synthesis activator provides a stimulating effect on TNF-α production in the mouse with Colon 26 carcinoma, thereby inhibiting tumor growth.

As stated above in detail, the ATP synthesis activator of the present invention can promote ATP synthesis in the body because it comprises, as an active ingredient, a mixture of a plurality of herbs having an ion-exchange capacity. Accordingly, the ATP synthesis activator can be used to ameliorate a symptom caused by lack of ATP.

What is claimed is:

1. An adenosine triphosphate (ATP) synthesis activator comprising, as an active ingredient, a mixture of herbs containing 8–12% by weight of thyme, 8–12% by weight of rosemary, 8–12% by weight of turmeric, 13–17% by weight of fennel, 13–17% by weight of grape seeds, 8–12% by weight of dandelion, and 25–35% by weight of *Acanthopanax senticosus*, based on the total weight of the mixture which is set to 100% by weigh.

* * * * *